(12) United States Patent
Boss et al.

(10) Patent No.: US 10,568,501 B2
(45) Date of Patent: Feb. 25, 2020

(54) APPARATUS FOR MODELLING OCULAR STRUCTURES

(71) Applicant: Novartis AG, Basel (CH)

(72) Inventors: Daniel Boss, Zurich (CH); Michael Mrochen, Eglisau (CH); Andrew Nolan, Louth (IE); Pav Zakharov, Volketswil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/030,104

(22) Filed: Jul. 9, 2018

(65) Prior Publication Data

US 2018/0310819 A1 Nov. 1, 2018

Related U.S. Application Data

(63) Continuation of application No. 15/091,615, filed on Apr. 6, 2016, now Pat. No. 10,016,125.

(30) Foreign Application Priority Data

Apr. 15, 2015 (EP) ..................................... 15163726

(51) Int. Cl.
| | | |
|---|---|---|
| *A61B 3/14* | (2006.01) | |
| *A61B 3/00* | (2006.01) | |
| *A61B 3/10* | (2006.01) | |
| *A61B 3/113* | (2006.01) | |
| *A61B 3/103* | (2006.01) | |
| *G01B 9/02* | (2006.01) | |

(52) U.S. Cl.
CPC ............ *A61B 3/0025* (2013.01); *A61B 3/102* (2013.01); *A61B 3/103* (2013.01); *A61B 3/113* (2013.01); *G01B 9/02091* (2013.01)

(58) Field of Classification Search
CPC ....... A61B 3/0025; A61B 3/102; A61B 3/103; A61B 3/113
USPC ........... 351/200, 205, 206, 209–22, 243–246
See application file for complete search history.

(56) References Cited

FOREIGN PATENT DOCUMENTS

| | | | |
|---|---|---|---|
| EP | 2762060 A2 | 8/2014 | |
| EP | 2762060 A3 | 12/2016 | |
| JP | 1836953 | * 3/2007 | ............... A61B 3/12 |

* cited by examiner

*Primary Examiner* — Brandi N Thomas

(57) ABSTRACT

An apparatus for motion compensated modelling of a parameter of an eye, comprising: a first measuring means for measuring a plurality of position parameters of the eye with respect to an optical reference coordinate system of the apparatus; a second measuring means for measuring an interference signal at a plurality of optical reference coordinates, wherein the measurement of the plurality of position parameters and measurement of the interference signal are time synchronised; means for correcting the interference signal to account for a displacements of a parameter of the plurality of position parameters; and means for modelling the eye parameter based at least in part on the corrected interference signal.

13 Claims, 7 Drawing Sheets

US 10,568,501 B2

APPARATUS FOR MODELLING OCULAR STRUCTURES

TECHNICAL FIELD

The technology described herein relates to ocular modelling and in particular motion compensated modelling of a parameter of an eye.

BACKGROUND ART

Ocular procedures often modify one or more structures of the eye, such as the cornea, lens or retina. Some procedures involve removing or replacing one or more structures of the eye, or adding an implant. For example, lens replacement surgery involves removing a patient's existing lens and replacing it with a new lens. Some procedures, such as laser vision correction surgery, do not remove or replace existing structures of a patient's eye, or add an implant to the eye, but rather reshape existing structures. Regardless of the type of modification being made (e.g. removal, replacement, insertion, or alteration), the optical performance of the eye is altered by adjustments made to the structures of the eye. Therefore in order to accurately model the structure of any eye, it is necessary to determine the ocular parameters of that eye. These parameters include shape, thickness and refractive index of ocular structures such as the cornea, the lens, the retina, or any other structure of interest.

Measuring parameters such as curvatures, or shapes of surfaces, or thickness of elements within a patient's eye is traditionally carried out using variations of ultrasound Optical Coherence Tomography (OCT) or Optical Low Coherence Reflectometry (OLCR), Purkinje or Scheimpflug imaging systems.

With living subjects and taking into account the precision of the measurements required it is necessary to introduce a level of movement compensation. Solutions for movement compensation are introduced in US 2012140175 A (CARL ZEISS MEDITEC, INC) 24 Jan. 2012, US 2013188140 A (CARL ZEISS, MEDITEC, INC) 17 Jan. 2013, US 2011267340 A (UNIV FRIEDRICH ALEXANDER ER [DE]; MASSACHUSETTS INST TECHNOLOGY [US]) 29 Apr. 2011, EP 2198771 A (OPTOPOL TECHNOLOGY, SA) 2 Dec. 2012, and WO 2010/101162 A (CANON KK [JP]; NUMAJIRI YASUYUKI [JP]; YAMADA KAZURO [JP]; HIROSE FUTOSHI [JP] 24 Feb. 2010. Additionally, US 2012249956 A (NARASIMHA-IYER HARIHAR [US]; EVERETT MATTHEW J [US]; ZEISS CARL MEDITEC INC [US]), WO 2010/149420 A (SIEMENS AG [DE]; KLEINFELD JENS [DE]; KLUGE ANDRE [DE]; MEISL JUERGEN [DE]; TUESCHEN SABINE [DE]; WO) 26 Mar. 2009 US 2013195336 A (UCHIDA HIROKI [JP]; CANON KK [JP]) 30 Aug. 2012 apply additional data processing and scan patterns to movement compensation to account for movement of the subject/patient's head. US 2009091766 A (CANON KK [JP]) 30 Aug. 2008 and DE 102009022958 A (ZEISS CARL MEDITEC AG [DE]) 28 May 2009 also acquire simultaneous fundus images in order to track eye movement and thus compensate for same in order to improve the determination of optical parameters.

To further improve the determination and accuracy of optical measurements using OCT/OLCR, attempts have been made to combine measurements made using these systems with additional measurement/movement detection to correct motion artefacts. Advances have been made in corneal vertex position detection through the use of additional measuring modality to provide accurate axial length measurement.

U.S. Pat. No. 5,387,951 B (TOPCON CORP) 7 Mar. 1995 discloses an apparatus for intraocular length measurements which avoids errors in measurement caused by the movement of a subjects head. By concurrently measuring the axial movement of the eye during the measurement process, the actual eye length can be calculated by adjusting the apparent length by the amount of axial movement. A disadvantage of this system is that motion correction applies only to axial length measurement.

US 2007076217 (CARL ZEISS MEDITEC, INC) 5 Oct. 2005 is directed to the use of optical coherence tomography for eye length measurement. A second OCT device is used to correct measurements made by the first OCT device. As with U.S. Pat. No. 5,387,951 this disclosure is only directed to axial length correction rather than a total A-scan. Furthermore, only z-axis displacement is accounted for in measurements and corrections.

US 2010014051 A (SIS AG SURGICAL INSTR SYSTEMS) 24 Jul. 2008 combined interferometric techniques to determine a relative position of the retina of the eye and uses a second non-interferometric technique to determine a relative position of the cornea and uses these measurements to determine the axial length of the eye. As previously, only z-axis displacement is accounted for. No motion compensation A-scan measurements are possible.

WO 2014/043517 A (UNIV JOHNS HOPKINS [US]) 13 Sep. 2013 is also directed to a motion compensated OCT and feedback system which provides for correction of deviation based on cross correlation of adjacent scans. However, this document does not provide for absolute motion tracking.

WO 2010/010116 A (BIOGASOL IPR APS [DK]; MIKKELSEN MARIE JUST [DK]; YAO SHUO [DK]) 29 Jul. 2009 implements the Scheimpflug principles in corneal vertex position detection with additional measuring modality. This document provides a means for measuring corneal vertex position (x, y, z) however, provides only for axial eye motion, i.e. z-axis compensation.

WO 2009/149953 A (ZEISS CARL MEDITEC AG [DE]; BUBLITZ DANIEL [DE]; KRAMPERT GERHARD [DE]; HACKER MARTIN [DE]) 12 Jun. 2009 uses first and second OCT measurements to compensate for a complete A-scan OCT, but again only provides for active eye motion compensation, is z-axis compensation.

It is therefore an object of the present invention to implement an improved compensation system and method for eye movement compensated measurements of multiple ocular surface locations. In systems such as those described above where two methods of measurement are implemented compensation is only for axial length measurements and compensation is for z-axis displacement. It is an object of the present invention to provide a more accurate system and namely a measurement system that is not influenced by eye motions.

SUMMARY OF INVENTION

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning consistent with the particular concepts disclosed herein.

The invention as described herein includes an apparatus for motion compensated modelling of a parameter of an eye, comprising:
- a first measuring means for measuring a plurality of position parameters of the eye with respect to an optical reference coordinate system of the apparatus;
- a second measuring means for measuring an interference signal at a plurality of optical reference coordinates, wherein the measurement of the plurality of position parameters and measurement of the interference signal are time synchronised;
- means for correcting the interference signal to account for a displacements of a parameter of the plurality of position parameters; and
- means for modelling the eye parameter based at least in part on the corrected interference signal.

This integrated measurement system for ocular modelling allows for measurements of the eye that are independent of eye motions of a patient or are not influenced by eye motions. The first measuring means provides instantaneous measurement of eye position parameters, while the second measuring means provides measurements of optical path length differences.

The plurality of position parameters may include lateral displacement along an x axis of the optical reference coordinate system, lateral displacement along a y axis of the optical reference coordinate system and axial displacement along a z axis of the optical reference coordinate system.

The plurality of position parameters may include cyclo-rotation around the z-axis.

The plurality of position parameters may include rotation around the x axis and rotation around the y axis.

The provision of instantaneous measurements of the eye position in a plurality of planes facilitates accurate motion compensation as eye roll is taken into account. The combination of the position parameters for eye parameter/ocular modelling provides for more accurate eye parameter reconstruction. For example where the second measuring means is an OCT system providing a time domain A-scan, and the first measuring means is a Purkinje imaging system or other ocular coherence tomography or Scheimpflug imaging system, the apparatus as claimed allows for the whole A-scan to be compensated, and not only the OPD between two surfaces as in a dual beam OLCR implementation. The motion compensated A-scan takes into account lateral eye movement and also axial displacement. The combination of the features allows for a relaxation in scanning. For example if the second measuring means is an OCT system, a slower scanner can be used as it is not essential that the patient stay still as the OCT measurements can be motion compensated.

The modelled eye parameter may comprise a shape, thickness, distance, or position of the eye.

Means for determining a displacement may comprise means for interpolating between measurements of the plurality of position parameters.

The embodied apparatus may further comprise means for determining a reference location of the second measuring device and means for correcting said reference location based on the measured position parameters.

The means for correcting may further comprise means for correcting an optical path length based on a difference in an optical path length between an off-axis ray-traced path length and a path length along the z axis of the optical reference coordinate system.

The first measuring device may further comprise means for measuring a position parameter based on a retinal reflex.

The optical path length may be iteratively corrected.

The first measuring device may comprise means for illuminating a targeted ocular surface with a least one incident light beam and means for direct at least two light beams returning from the illuminated ocular surface to an image forming device.

The ocular surface may include an anterior corneal surface, a posterior corneal surface, an anterior lens surface, a posterior lens surface or a retinal surface.

The first measuring means may be selected from a list including a Purkinje Mirror Imaging device, an Optical coherence Tomography Device or a Scheimpflug Imaging System and the second measuring means comprises an optical coherence device. The second measuring means may be selected from a list including a Purkinje Mirror Imaging device, an Optical coherence Tomography Device or a Scheimpflug Imaging System.

The apparatus may further comprise means for determining refraction at the ocular surface and correcting the modelled eye parameter based on the determined refraction.

A further embodiment of the invention includes a method for motion compensated modelling of a parameter of an eye, comprising:
- measuring a plurality of position parameters of the eye with respect to an optical reference coordinate system of the apparatus;
- measuring an interference signal at a plurality of optical reference coordinates, wherein the measurement of the plurality of position parameters and measurement of the interference signal are time synchronised;
- correcting the interference signal to account for a displacements of a parameter of the plurality of position parameters; and
- modelling the eye parameter based at least in part on the corrected interference signal.

The plurality of position parameters may include lateral displacement along an x axis of the optical reference coordinate system, lateral displacement along a y axis of the optical reference coordinate system and axial displacement along a z axis of the optical reference coordinate system.

The plurality of position parameters may include cyclo-rotation around the z-axis.

The plurality of position parameters may include rotation around the x axis and rotation around the y axis.

The modelled eye parameter may comprise a shape, thickness, distance, or position of the eye.

Determining a displacement may comprise interpolating between measurements of the plurality of position parameters.

The embodied method may further comprise determining a reference location of the second measuring device and correcting said reference location based on the measured position parameters.

Correcting may further comprise correcting an optical path length based on a difference in an optical path length between an off-axis ray-traced path length and a path length along the z axis of the optical reference coordinate system.

The method may further comprise measuring a position parameter based on a retinal reflex.

The optical path length may be iteratively corrected.

The method may further comprise illuminating a targeted ocular surface with a least one incident light beam and means for direct at least two light beams returning from the illuminated ocular surface to an image forming device.

The ocular surface may include an anterior corneal surface, a posterior corneal surface, an anterior lens surface, a posterior lens surface or a retinal surface.

The method may further comprise determining refraction at the ocular surface and correcting the modelled eye parameter based on the determined refraction.

A further embodiment of the invention includes a system comprising the apparatus according to any of claims 1 to 13 and further comprising a camera.

There is also provided a computer program comprising program instructions for causing a computer program to carry out the above method which may be embodied on a record medium, carrier signal or read-only memory.

BRIEF DESCRIPTION OF DRAWINGS

Various non-limiting embodiments of the technology described herein will not be described with specific reference to the following figures. It should be appreciated that the figures are not necessarily drawn to scale.

DESCRIPTION OF EMBODIMENTS

The aspects of the technology mentioned above, as well as additional aspects, will now be described in greater detail. The aspects may be used individually, all together or in any combination of two or more, as the technology is not limited in this respect.

Figure 1:
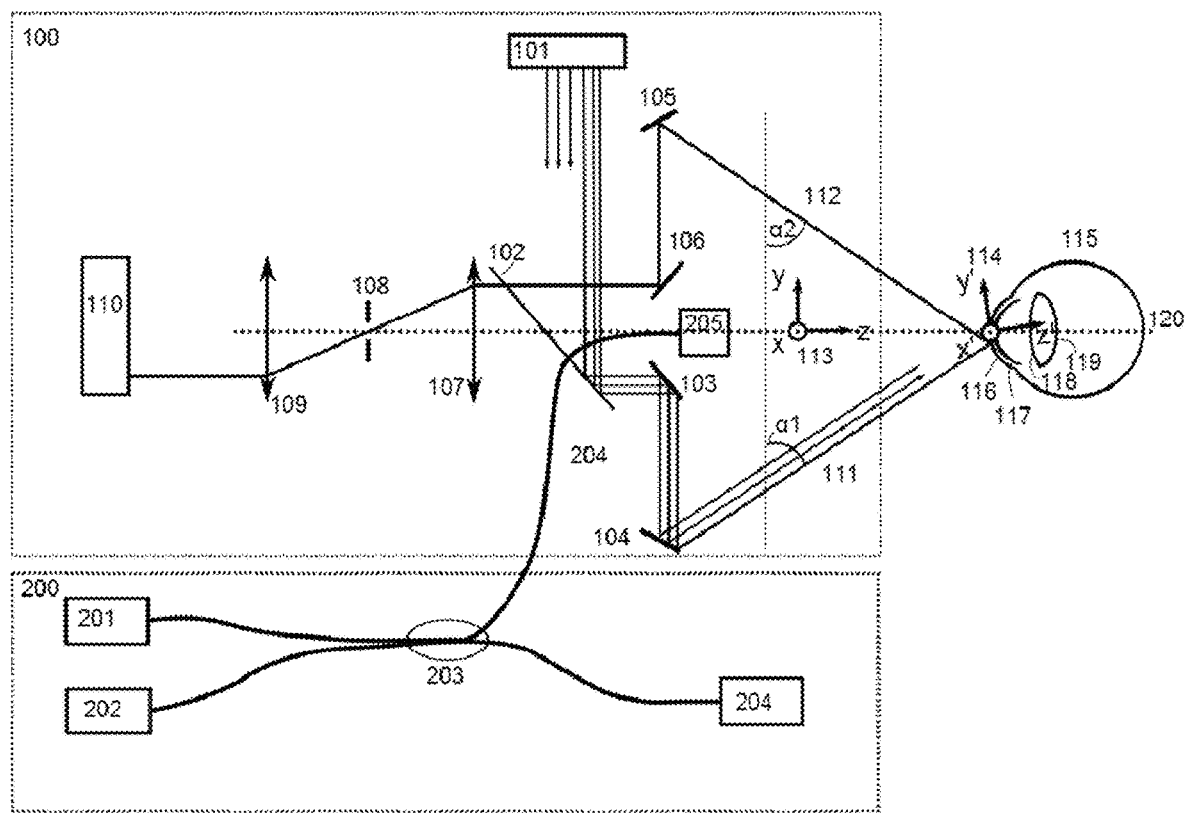
FIG. 1 depicts a configuration of an optical system combining a Purkinje Mirror Imaging modality (PMI) and an OLCR measurement apparatus for ocular measurements in accordance with an embodiment of the present intervention.

The system shown in FIG. 1 illustrates a configuration of an optical system combining a Purkinje Mirror Imaging (PMI) Modality 100 and an Optical Low Coherence Reflectometry (OCLR) 200 for ocular measurements of structures of interest in accordance with the present invention. A structure of interest may be a complete structure (e.g., a lens) or a surface (e.g. the front of the lens) and a parameter may be the shape, thickness or refractive index of the structure of interest. Any of these parameters may be of interest either as an ultimate result or a means for determining other parameters or for both purposes. For example, the shape of the cornea may be of interest as an end result for modelling the cornea, but may also facilitate the determination of the refractive index of the cornea.

The Purkinje Mirror Imaging Modality 100 comprises light source(s) and optics 101 which are arranged to emit collimated light. The collimated light illuminates the surface of interest. Illumination of the surfaces can be done with any wavelength beam of any type, be that coherent laser light, partially coherent LED light or an incoherent broadband source. In a preferred embodiment, wavelengths are chosen such that water and tissue absorption in the eye are minimized. Wavelengths in the range of 400 to 1300 nm (broad) and preferably 700-900 nm are optimal.

A beam splitter 102 reflects illuminating light into at least two illumination channels. Light paths 111, shown in FIG. 1, are illustrative of illumination through an illumination channel consisting of outer and inner mirror 103, 104. These mirrors are arranged to direct illuminating beams 111 onto an eye 115 at a fixed illumination angle $\alpha 1$ with respect to an optical reference coordinate system 113 (x, y, z) as shown in FIG. 1. These mirrors may be rod mirrors for example. However, it will be appreciated that they are not restricted as such and may also include any reflective element including a combination of prisms with or without mirrors or glass cones.

When the illuminating beams fall on the mirrors they are directed to ocular surfaces 116, 117, 118, 119, 120 from which they are then reflected. As will be appreciated ocular surfaces include an anterior corneal surface 116, posterior corneal surface 117 anterior lens surface 118, posterior lens surface 119 and retinal surface 120.

Light reflected from the ocular surfaces is collected by at least two imaging channels onto at least one image forming device 110.

An example of such an imaging channel is shown by light path 112 which illustrates the image formation through an imaging channel. Reflected light from the anterior corneal surface 116 is collected by an outer mirror 105 and an inner mirror 106. This reflected and collected light is then transmitted through the beam splitter 102.

To achieve a telecentric image formation on the image forming device 110 of the reflections from the ocular surfaces (Purkinje reflections) a pin hole 108 placed at a focal points of two lenses 107 and 109. In this imaging channel, image formation occurs for reflected rays making a fixed angle $\alpha 2$ with respect to the optical system coordinate system 113.

Illuminating channels used to illuminate the eye with collimated beams at a fixed angle $\alpha 1$ are used at the same time as imaging channels to transmit light reflected at a fixed angle $\alpha 2$ onto the image forming device 110.

A suitable configuration for such a PMI unit is described in WO 2012/130818 A (NAT DIGITAL RES CT [IE]) 26 Mar. 2012 which is incorporated herein by reference in its entirety. The system described therein is referred to as a "Mirricon" system. In the Mirricon system an illuminating beam from a collimated source is injected into the system to illuminate mirrors located on the optical axis. When rays from the source fall on the mirrors these rays are then reflected to a system of meridional flat mirrors. The Mirricon system is configured both for the illumination of the eye with collimated beams off axis and also for imaging the Purkinje reflections. The returning light passes back to the imaging forming device as described herein.

In combination with the PMI unit 100, an OCT imaging modality unit/Eye scanning unit 200 is provided. This unit incorporates a light source 201, photodetector 202, light coupler 203, reference light beam with reference mirror 204, and an object light beam 205. It will be appreciated that OCT imaging modality may be time domain OCT, optical coherence reflectometry, OLCR, or Spectral Domain OCT using a broadband source or swept source. Unless specifically mentioned herein OCT may refer to any of these systems.

Figure 2:
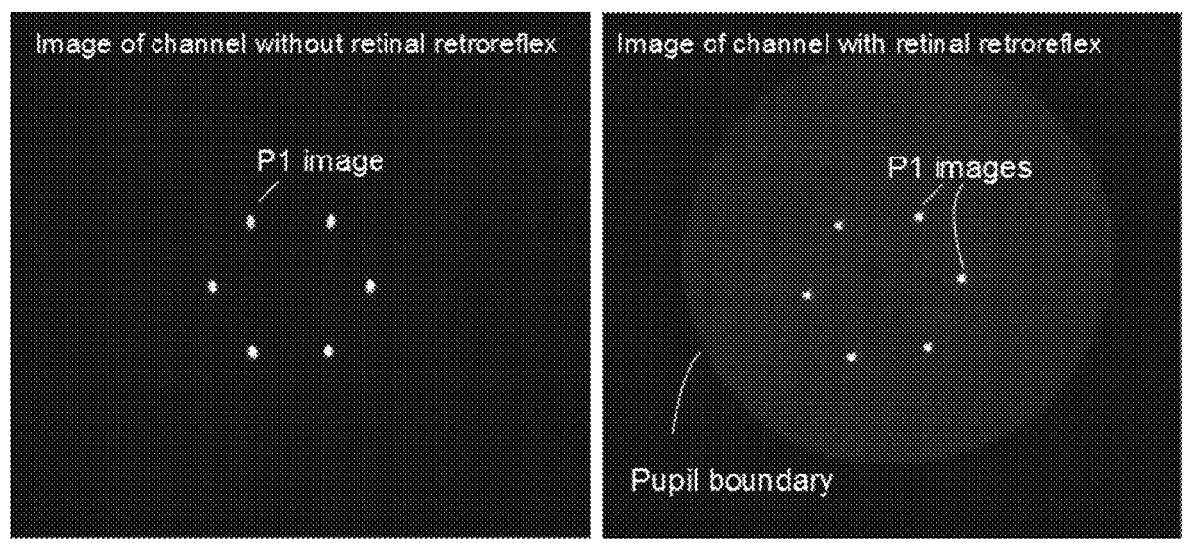
FIG. 2 depicts features in illumination channels for extraction in accordance with the present invention.

In accordance with the system of FIG. 1 the imaging forming device 110 captures and stores images which contain information on the spatial locations of Purkinje reflections from illuminating beans in the at least two illuminating channels and images through the at least two imaging channels. It will be appreciated that generally at least four Purkinje images reflected from incident light of an illumination channel and transmitted through an imaging channel are usually visible, for example the first Purkinje image (P1) is the reflection from the anterior corneal surface. The second Purkinje image (P2) is the reflection from the posterior corneal surface. The third Purkinje image (P3) is the reflection from the anterior lens surface. The fourth Purkinje image (P4) is the reflection from the posterior lens surface Further, the image forming device 110 captures light emanating from an illumination channel that is retro-reflected at the retinal surface 120 and is transmitted back through the illumination channel onto the image forming device 110. As shown in FIG. 2, the boundaries of the areas of the retinal reflex is indicative of the pupil boundary imaged through the imaging channel onto the image forming device. The images shown in FIG. 2 are illustrative of the pupil boundaries without and with retinal retroflex. The levels of illumination for the p1 images differ in both cases.

Parameters of the eye may include shape, thickness, distances, position of the eye and refractive index of the ocular structures of the eye. While some of the parameters listed above are intrinsic to the eye it will be appreciated that measurements such as position of the eye are derived from measurements of other parameters. Measurement of any one of shape, thickness and/or refractive index of an ocular structure of interest may depend to some extent on the directional changes which light employed by the measurement technique undergoes while passing through any ocular structures preceding the structure of interest. Thus, according to one aspect of the technology, measurements of shape thickness, and/or refractive index of ocular structures may be corrected to account for the dependence of the measured values of other parameters for that structure, as well as on any of the parameters of the preceding structures.

To reconstruct any of the eye parameters, the information collected and stored at the image forming device 110 is used to determine features including Purkinje image locations and pupil boundary locations based on the PMI Image Acquisition containing images of at least two image channels collecting reflections from the at least two illumination channels.

Reconstruction of any parameter of the eye may be performed using reverse ray-tracing through the modelled optical system. In such a system, rays are traced back from the detected locations of a detected feature on the image forming device 110 through the image channel onto the ocular surface containing the particular feature where it is reflected back at a certain angle. It will be appreciated that this angle must coincide with the angle of illumination a1 shown in FIG. 1. If these angles do not coincide, the initial parameter of the modelled subject eye is altered until the angle of the reference plane matches the illumination angle α1. Accordingly, an angle constraint is obtained for each detected Purkinje location. The difference between the known angle of illumination a1 and the reconstructed angle enters a merit function, i.e., the merit function is constructed from the multiple angle constraints from each detected Purkinje image. The optical path differences (OPD) between the ocular surfaces obtained from optical coherence peak positions is used as an additional constraint that can enter the merit function. In a preferred embodiment reconstruction is performed using an iterative optimization method. Parameters of the subject eye are altered until a minimum of the merit function is achieved. Examples of optimization methods include a damped least squares algorithm (DLS) or an Orthogonal Descent (OD) algorithm. The DLS algorithm for example uses numerically computed derivatives to determine a direction in solution space which produces an optimal configuration with a lower merit function. OD in contrast, uses an ortho-normalization of the variables and discrete sampling of solution space to reduce the merit function. The OD algorithm does not compute numerical derivatives of the merit function.

For parameters, such as anterior corneal parameters, including eye position, reconstruction is also possible based on matching ray positions from opposing spots. For example, given two channels A and B where both are simultaneously illuminated B, in a first step A is illuminated and B is imaged and in a second step B is illuminated and A is imaged. Based on an assumption that the beams take the same path in opposite directions positions of the rays can be matched to forma a merit function. It will be appreciated that such a configuration is suitable for anterior cornea or eye position reconstructions. If the sequential illuminations are sufficiently fast to be considered instantaneous then the above described method is also applicable to the anterior cornea. Eye position for example, may be determined with respect to the optical system reference axis. The system reference axis may be the central axis of the OCT system or any other defined reference axis, such as reference axis 113.

Figure 3:
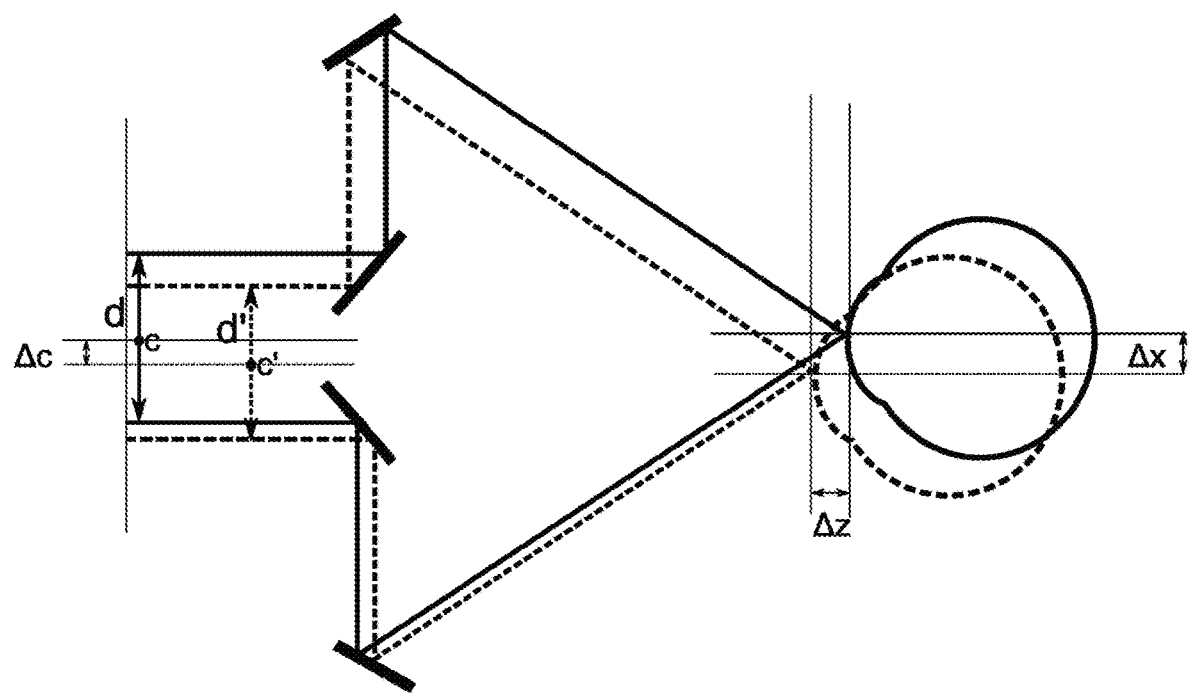
FIG. 3 illustrates translational eye position measurement from P1 spot locations

In an additional or alternative embodiment, eye position measurements may be determined directly from detected features. It will be appreciated that this is without an optimization procedure. As an example, lateral and axial position changes are directly infer-able from measured P1 spot locations. These spot locations emanate from opposing illumination channels and imaged by opposing imaging channels on the camera plane. FIG. 3 shows an axial displacement $\Delta z$ and a lateral displacement $\Delta x$ of the eye. This further shows the changes in spot positions in a virtual plane conjugate to the camera plane. The displacement $\Delta z$ of the eye along the optical axis is proportional to the change in distance between the spots in opposing illumination channels $\Delta d = d - d'$. The displacement $\Delta x$ within the x-y plane is proportional to the displacement of the centre of gravity $\Delta c$ of the spots from opposing illumination channels. The constant relation between $\Delta d$ and $\Delta z$, and $\Delta c$ and $\Delta z$ is determined by the geometry of the PMI configuration.

It will further be appreciated that P4 and the pupil centre positions derived from the pupil boundary positions can also be used for eye position determination.

Figure 4:
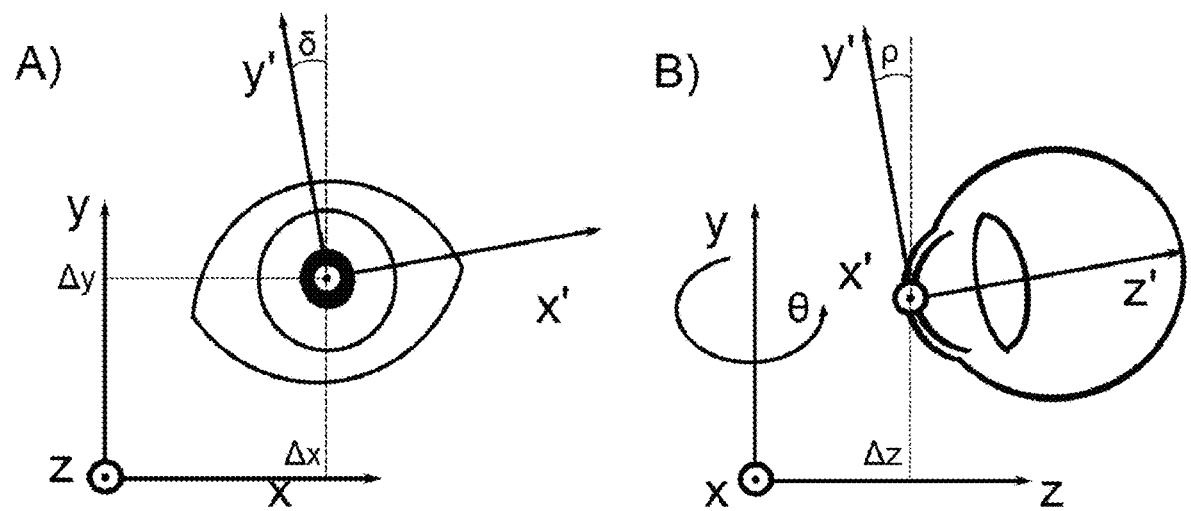
FIG. 4 is illustrative of the range of eye movements measurable with PMI in accordance with the present invention, namely 3 translational and 3 rotational degrees of freedom of eye motion.
Figure 5:
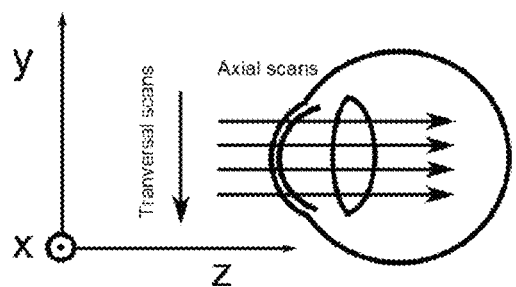
FIG. 5 shows scanning measurement principles used in OCT

FIG. 4 depicts the eye position parameters that can be reconstructed from a PMI acquisition with respect to an optical system reference axis as indicated. These eye position parameters include lateral displacements $\Delta x$, $\Delta y$ which are shown along the x, y axis respectively. The parameters also include axial displacement $\Delta z$ which is indicated along z-axis. In addition, cyclorotation δ is indicated where δ is rotation around z-axis. An additional parameter p shown in FIG. 2b and is representative of rotation around x-axis (eye roll movement). Rotation around y-axis (eye roll movement) is represented by the symbol e. It will be appreciated that one or more or any combination of these parameters can be reconstructed or determined. In accordance with the present invention and as depicted in FIG. 5, A scans or Axial scans and B scans or transversal scans are performed. These scans are time dependent. Geometrical reconstruction is dependent on the displacement of the eye due to eye motion.

Figure 6:
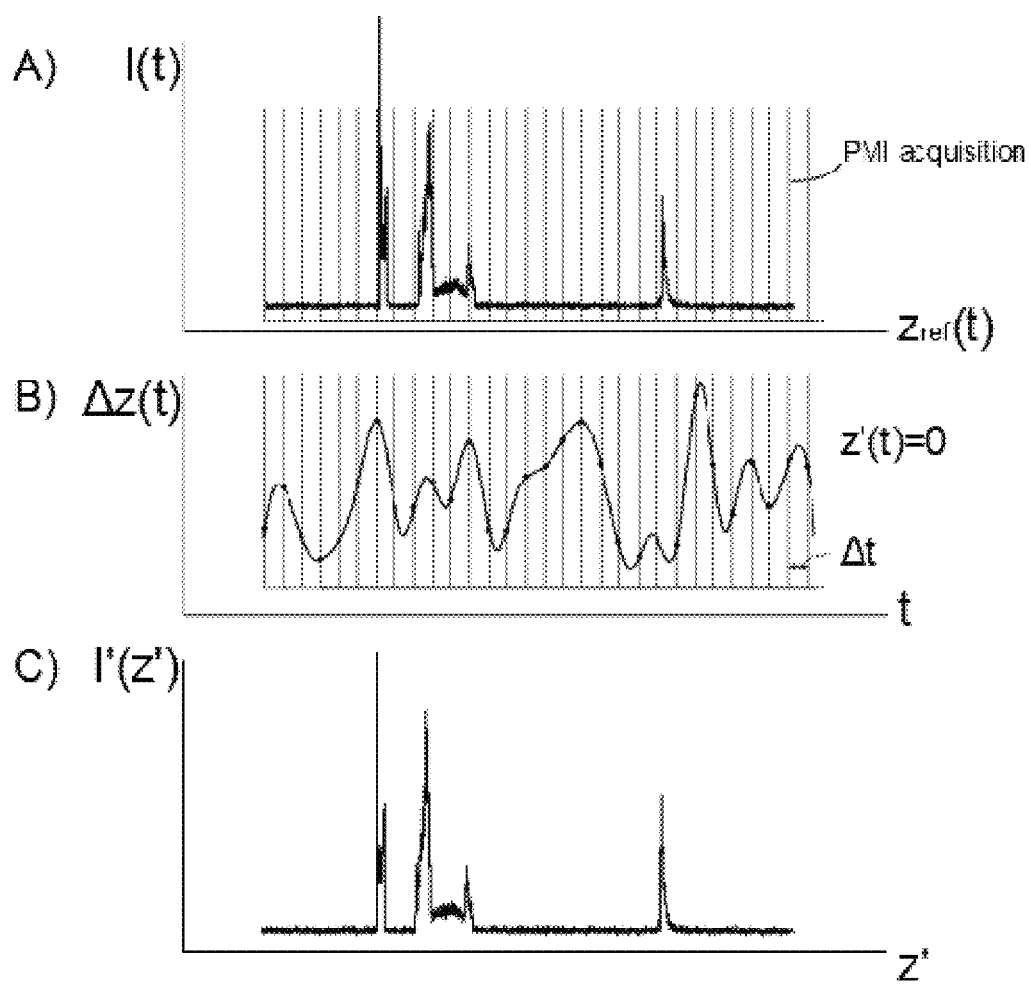
FIG. 6 depicts axial motion compensation in OCT-A scans using PMI tracked eye position.

The graphs of FIG. 6 are illustrative of axial motion compensation in a TIME domain OCT/OLCR axial scan at a given lateral position, x, y in the optical system reference axis.

The interference signal detected on the photodetector 202 of the OCT imaging modality 200 is filtered to extract an envelope signal I(t) as a function of time t of said interference signal as the reference mirror 204 is displaced by a known distance $z_{ref}(t)$ with respect to the optical system reference axis (cf. FIG. 6A)

For example, with an OCT scan in accordance with the present invention, for each measurement of an eye, 32 interferograms may be acquired. 32 is given herein as an example only. Envelope signals are reconstructed from the interferogram signals. In an example, the envelope of an interferogram may be reconstructed by filtering the raw interferogam with a Gabor filter. Such a filter is defined by two parameters, namely: the width of the Gaussian envelope and the frequency of sinusoidal modulation. The modulation frequency of the filter has to be matched with the frequency of the interferogram, f, which is defined by the speed of the scanner v, and the wavelength of the source λ:

$$f=2*v/\lambda$$

As an alternative, the envelope may be obtained by taking the absolute value of the complex analytic signal obtained from Hilbert transform of a Fourier filtered interferogram.

During the scanning period, the PMI modality 100 acquires images on the image forming device 110. Optionally these images may be obtained at a fixed temporal interval Δt. Where a fixed temporal interval is chosen it will be appreciated that this interval is chosen so that the acquisition frequency is higher than typical temporal frequencies of eye movements. Alternatively, a higher frequency may be chosen, such as for example, during an anterior chamber scan.

In the embodiment shown in FIG. 6, the acquisition of the PMI images is time synchronized with the measurement of the interference signal detected on the photodetector. This ensures that a PMI image acquisition corresponds to a known time point of the envelope signal I(t).

For example, from the measured PMI images the axial displacement Δz (Δ$t_i$) with respect to the optical system reference axis of the anterior cornea at the position [x',y',z']=(0,0,0) with respect to the subject eye reference axis 114 is reconstructed. Using the discrete set of axial displacement measurements Δz(Δ$t_i$), a function Δz(t) is obtained using an interpolation method (cf. FIG. 6B). It will be appreciated that this interpolation method can be a linear interpolation method, a nearest neighbour interpolation method or a spline interpolation method or the like.

An axial scanner position can then be expressed with respect to the subject eye coordinate system as $$z'_{ref}(t)=z_{ref}(t)+\Delta z(t)$$

With the knowledge of the function $z'_{ref}(t)$, the envelope signal I(t) can be expressed as a function I'(z') of the axial coordinate z' of the subject eye reference axis to obtain a compensated A-scan (cf. FIG. 6C) for axial eye displacements.

Multiple A-scans acquired sequentially at a given lateral position x,y in the optical system reference axis can be averaged by summing individual eye motion compensated A-scans.

Figure 7:
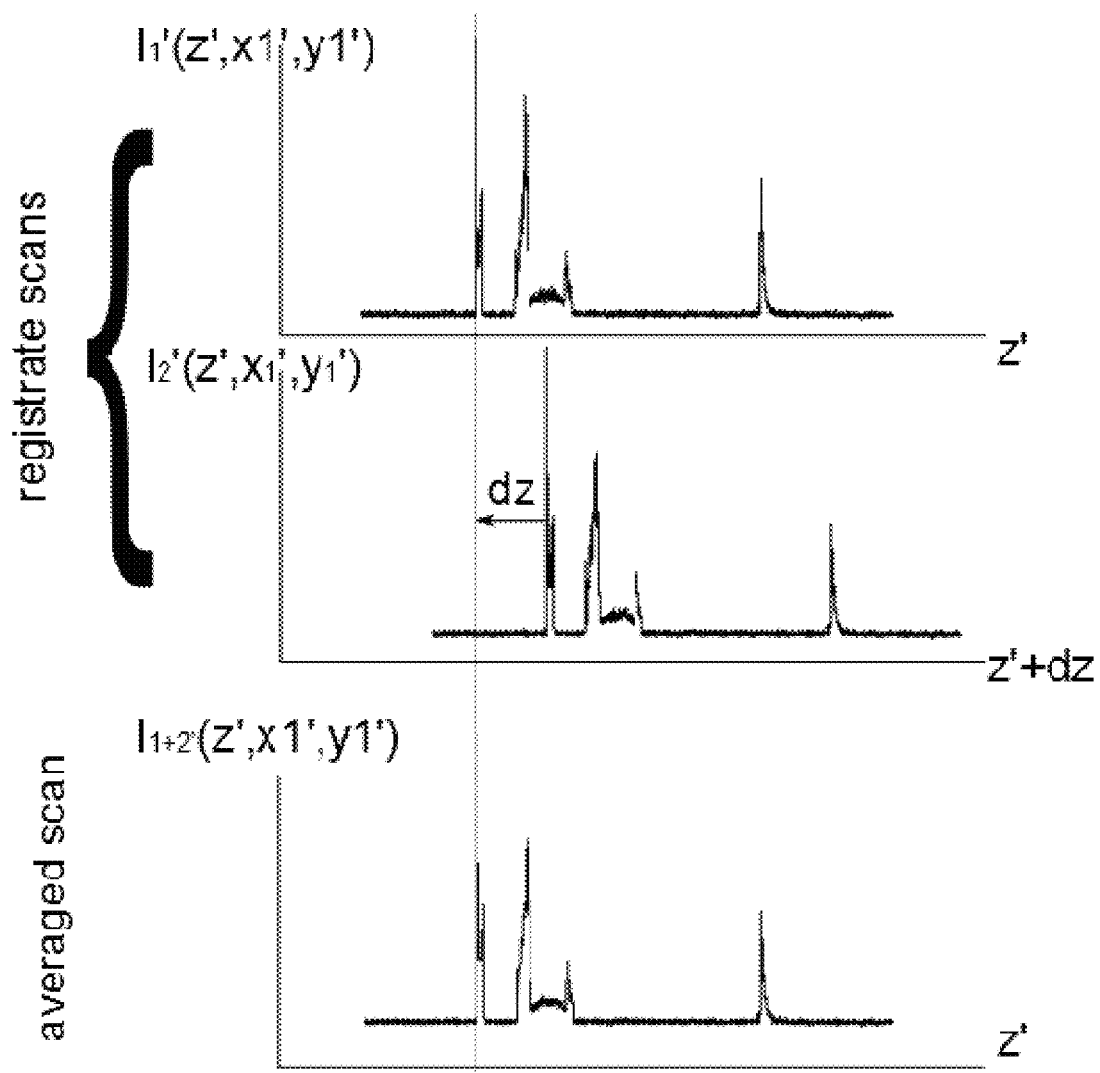
FIG. 7 illustrates registration applied to align multiple A-scans obtained at single measurement point within the eye coordinate system in accordance with the present invention.

If the absolute scanner position z(t) of the OCT modality is not known with respect to the optical system coordinate axis, i.e. only relative position changes of the scanner are known, it will be appreciated that the multiple eye motion compensated A-scans require re-alignment prior to averaging the multiple A-scans. This realignment can be performed by registration algorithms. Said registration algorithm can be based on maximizing the cross correlation amplitude between subsequent A-scan signals I(t) as shown in FIG. 7.

Motion compensation is further illustrated in the embodiments shown in FIGS. 8 to 11.

Figure 8:
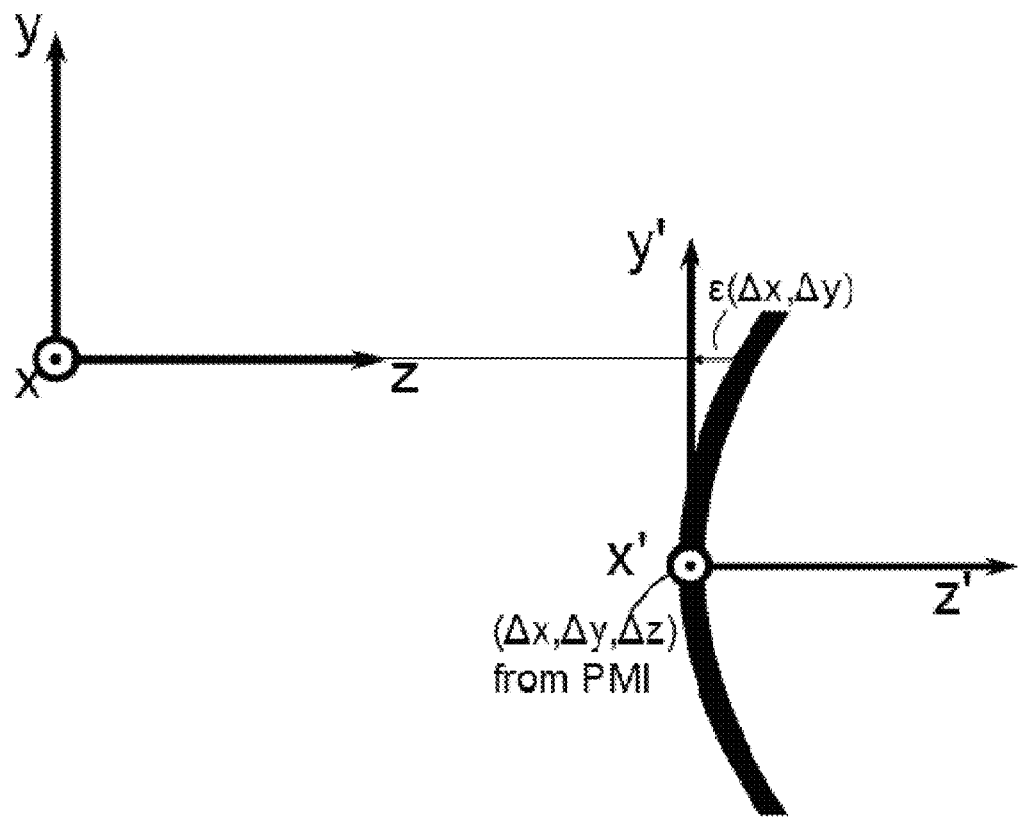
FIG. 8 shows off axis compensation in OLCR A scans for eye length measurements

In a first embodiment as shown in FIG. 8 X, Y motion compensation or off-axis compensation for OLCR axial length measurements is implemented. The motion compensation of a single OCT/OLCR A-scans for eye length measurements takes into account the lateral off-axis position (Δx, Δy) of the subject eye reference axis with respect to the system coordinate axis reconstructed from a PMI image acquisition. Such an embodiment is illustrated in FIG. 8 which shows the optical system reference axes, x, y and z with the optical measurement axis of the OCT along the z-direction and a subject eye coordinate system centred at the anterior corneal vertex position.

It will be appreciated that for accurate eye length measurements it is desirable to measure OCT A-scans when the optical system z-axis and the subject eye z'-axis are aligned.

For a laterally displaced eye coordinate system due to eye motions, a reflection of the OLCR measuring beam at the cornea occurs after the measuring beam travels an additional optical path length ε(Δx,Δy) that is dependent on the off-axis position (Δx,Δy).

To compensate for an off-axis position in the measurement of eye length, the reconstructed measurement of the axial displacement of the anterior cornea Δz(t) with respect to the optical reference system is corrected as $\Delta z_{corr}(t)=\Delta z(t)-\xi(\Delta x(t), \Delta y(t), \Delta z(t))$. A correction function ξ(x,y,z) can be derived from an average topography of the cornea of multiple eyes or from a corneal curvature measurement of the subject eye derived from measured PMI eye parameters.

It will be appreciated that the correction function ξ(x,y,z) further depends on the axial displacement of the scanner position z(t).

Figure 9:
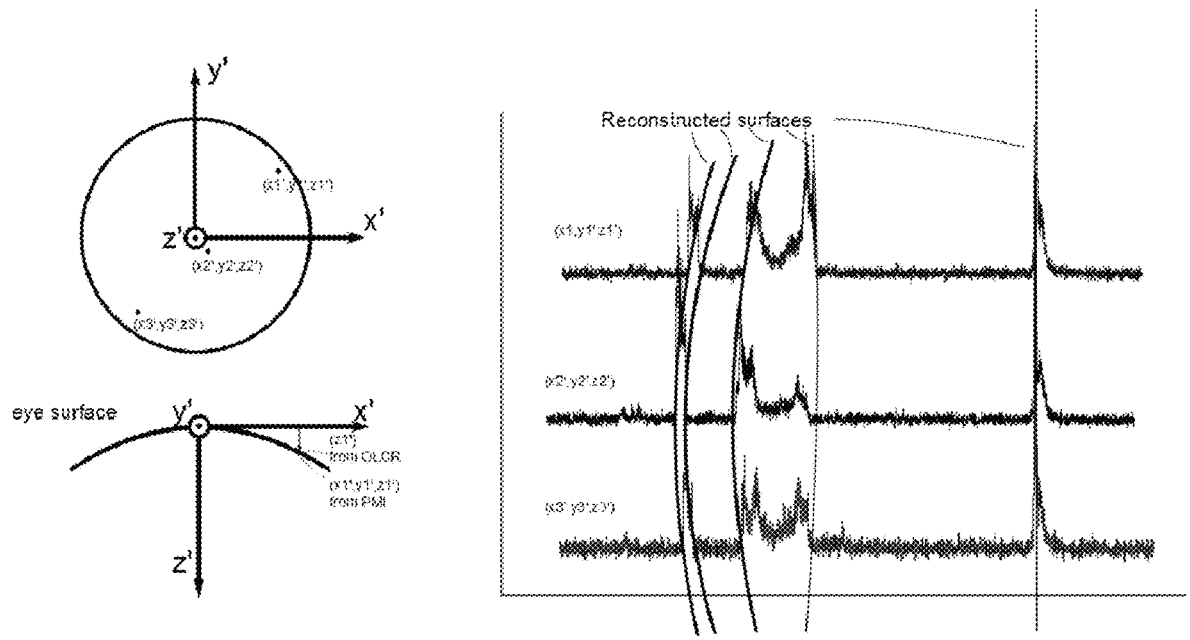
FIG. 9 demonstrates reconstruction of ocular surfaces based on a combination of PMI with multiple OCT measurement points within the eye coordinate system.

For scanner positions in the vicinity of the expected retina position the function ξ(x,y,z) equals to 0, such that no off-axis correction is added to the measured axial displacements Δz(t) when the OCT signal from the retinal surface is detected. The embodiment of the invention as shown in FIG. 9 is illustrative of a system which combines PMI and OLCR/OCT measured at off-axis positions XY. In this embodiment the OCT object beam measures at multiple measurement points within the eye coordinate system. Multiple measurements at different locations within the subject's eye coordinate system are taken using a transversal scanning (B-scan) of the OCT measuring beam. In an alternative, multiple measurements are taken at different locations within the subject eye coordinate system by allowing passive movements of the subject eye coordinate system with respect to the optical system coordinate. Such passive relative movements could occur due to eye movements or movements of a handheld implementation of a PMI/OCT measurement device.

The measuring location (x',y') of a reflection position of the OCT object beam on an ocular surface within the eye coordinate system can be calculated from the measuring location (x,y,z) within the optical system coordinate axes and the measured eye position parameters obtained from the PMI acquisition.

The axial displacement z' of said reflection position on said ocular surface within the eye coordinate system can be obtained either from the reconstructed eye parameters or from the measured peak position in the OCT scan. This thus offers novel constraints that can enter the merit function to more accurately reconstruct the eye parameters based on multiple measurement points within the eye coordinate system.

Iterative processes may be applied to calculate corrections which may be due to light propagation and refraction at a known surface point. For example, the surface of the eye may be reconstructed based on corrected OPD/OLCR/OCT signals. Derivation of these corrections may be implemented in an iterative process.

Figure 10:
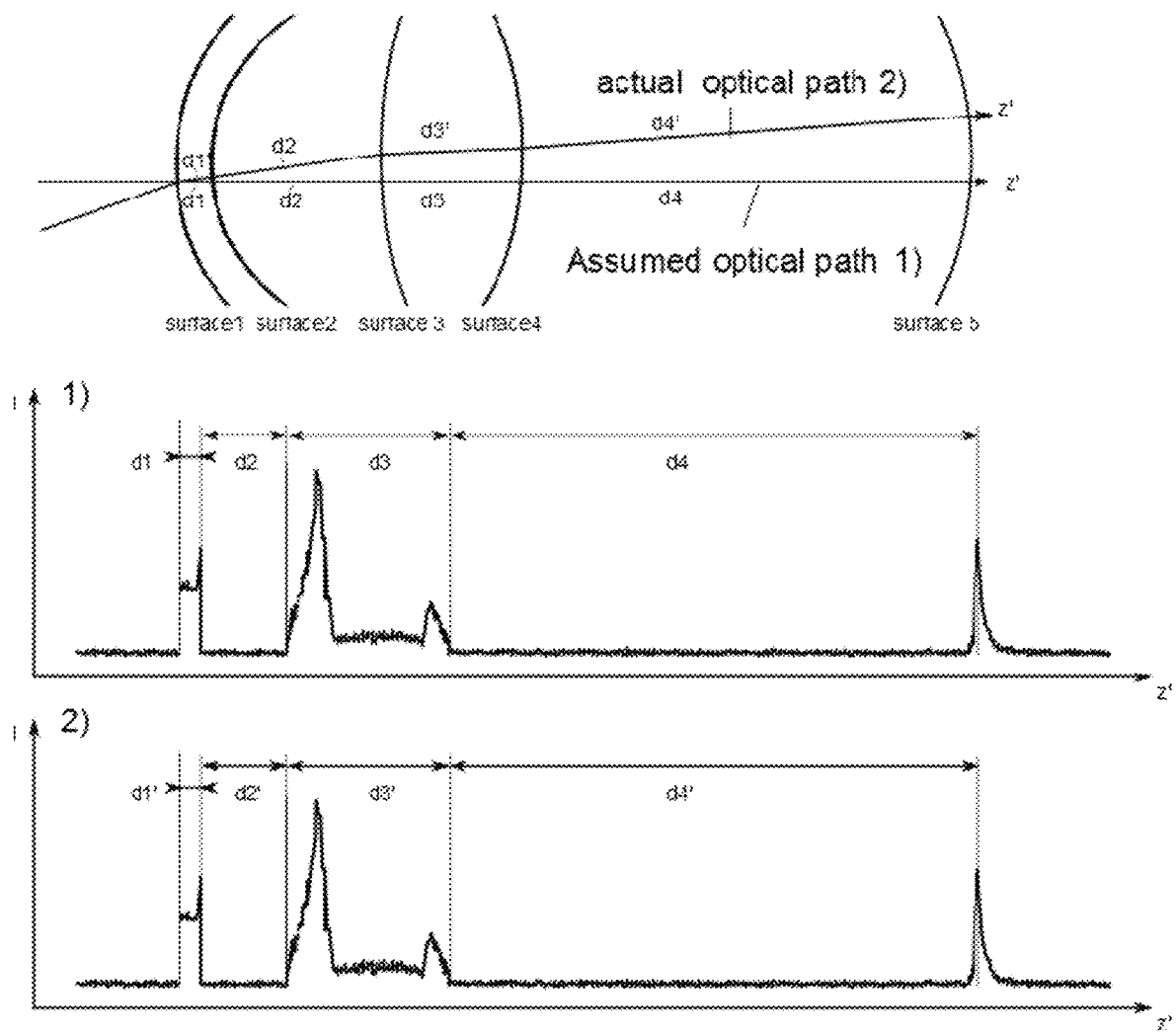
FIG. 10 illustrates the reconstruction of eye parameters taking into account refraction of the OLCR measuring beam within the subject eye in accordance with the present invention.

FIG. 10 details X, Y and eye roll movement compensation using the combination of PMI with OLCR whilst taking into account refraction at the ocular surface. This iterative reconstruction is therefore based on PMI in combination with OLCR peak positions and light propagation/refractions within the eye.

An actual optical path 2 and an assumed optical path 1 are shown in FIG. 10. Distances between surfaces of the eye along the assumed path 1 are shown as d1, d2, d3 and d4, with corresponding distances along the actual optical path shown as d1', d2', d3' and d4'. For example the distance between surface 1 and surface 2 along the assumed path is d1 and the corresponding distance along the actual path is shown as d1'.

For example, surface 1 may be the front surface of the cornea and surface 2 may be the back surface of the cornea. The distances d1 and d1' are therefore the assumed and actual distances between the front and back surface of the cornea. Surface 3 may be considered the front surface of the lens of the eye and surface 4 the back surface of the lens of the eye. The cornea and the lens are separated by a distance d2 and d2', i.e. the assumed and actual distance from the back surface of the cornea to the front surface of the lens. The distances d3 and d3' are between the front and back surfaces of the lens. Surface 5 may be the retina of the eye. Surface 5 is separated from the surface 4, or the back surface of the lens, by a distance d4 or d4'. As shown in the graphs of FIG. 7, the first graph is indicative of the surfaces on the assumed optical path and the second graph is indicative of the surfaces on the actual optical path.

In a first iteration of reconstruction, eye parameters are reconstructed using OPD values attributed to an assumed optical path 1 along the subject eye z'-axis.

In a second iteration, the OCT measuring beam is traced through the eye based on reconstructed eye parameters including eye position measurements ($\Delta x$, $\Delta y$, $\Delta z$, $\Theta$, $\rho$, $\delta$).

The optical path length $d_n'$ along the actual optical path 2 must correspond to the measured OCT distances. If it is not the case, the eye must be reconstructed with corrected OPD measurements $d_1 \ldots d_{n-1}$ (assumed distances) along the subject eye z'-axis.

Figure 11:
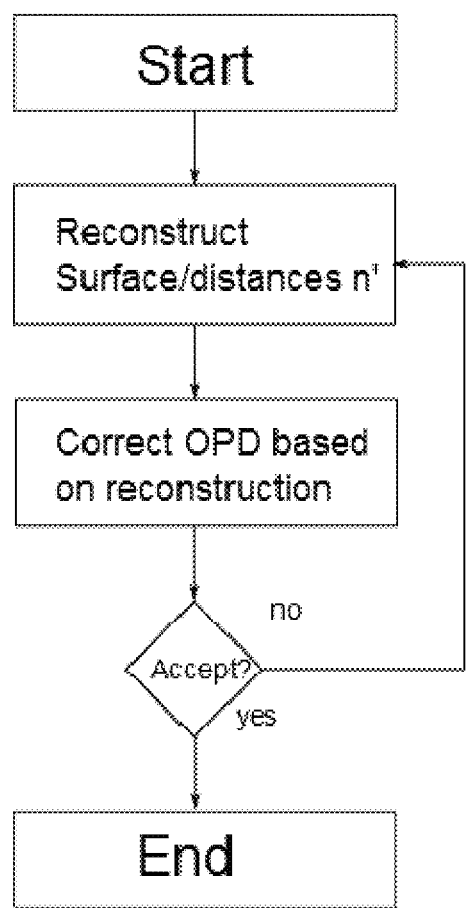
FIG. 11 shows an iterative process for reconstruction of ocular surface in accordance with the present invention

An exemplary iterative process is shown in FIG. 11.

For each ocular surface, n=1, 2, 3, 4, 5 eye parameters up to surface n are reconstructed 801 using OPD distance measurements $d_1 \ldots d_{n-1}$ as outlined above. In a first iteration the on-axis OPD distance measurement corresponds to the measured OLCR distance measurement $d_{n-1}$.

OLCR measurement beam are traced up to the relevant surface n based on reconstructed eye up to surface and eye position measurement ($\Delta x$, $\Delta y$, $\Delta z$, $\Theta$, $\rho$, $\delta$) thus defining a position with respect to system coordinate system at the time t that the peak of surface n as shown in FIG. 10 was measured.

The on-axis OPD distance measurement $d_{n-1}$ is then corrected 802. This correction is according to the difference between the traced and measured distance $d_{n-1}$. If the difference between the traced and measured distance $d_{n-1}$ is greater than a threshold the iterative process begins again at step 801. If the difference between the distances is less than or equal to a threshold, measurements may move to a new surface and the process is restarted for the new surface.

In a further embodiment a non-iterative reconstruction may also be implemented. In such an embodiment, eye reconstruction takes into account eye movements and refraction at ocular surfaces. In a first step the shape of the anterior cornea and the location and incidence of OLCR/OCT beam with regard to the eye coordinate system is reconstructed with PMI in an instantaneous fashion. PMI allows mapping of the OLCR/OCT A-scan signal emanating from the anterior corneal to the eye coordinate system and evaluating of the change of the incidence of the OLCR/OCT measuring beam occurring at the anterior corneal surface.

In a second step, posterior corneal surface is reconstructed based on the reconstructed anterior corneal surface, instantaneously acquired PMI P2 signals and corneal thickness OPD at the location of the OLCR/OCT A-scan signal emanating from the posterior corneal surface with respect to the eye coordinate system. The reconstructed posterior corneal surface allows the evaluation of the change of the incidence of the OLCR/OCT measuring beam at this surface.

In a third step, the anterior lens surface is reconstructed based on the reconstructed anterior and posterior corneal surfaces, the instantaneously acquired P3 signals and anterior chamber depth OPD at the locations of the OLCR/OCT A-scan signal emanating from the anterior lens surface with respect to the eye coordinate system. The reconstructed anterior lens surface allows the evaluation of the change of the incidence of the OLCR/OCT measuring beam. The posterior lens surface is similarly reconstructed.

Finally the OLCR/OCT A-scan signal emanating from the retinal surfaces can be mapped to the eye coordinate system by tracing the OLCR/OCT measuring beam through the reconstructed surfaces.

The invention and embodiments thereof as described herein provide for a combination of a PMI/OCT modality for reconstruction of eye parameters where the PMI modality is used for (passive, offline) movement compensation of OCT measurements. This provides for more accurate eye parameter reconstruction.

Furthermore eye movement compensated measurements of multiple ocular surface locations in a time-domain OCT A-scan are provided for (i.e. whole A-scan is motion compensated, not only OPD between two surfaces as in a dual beam OLCR implementation.

The embodiments described above also allow for motion compensated OCT A-scan for eye length measurement taking into account lateral eye movements ($\Delta x$, $\Delta y$) in addition to axial displacement $\Delta z$.

The increased accuracy of correction allows a relaxation of requirements for OCT/OLCR scanners in that a slower scanner may be implemented. It will be appreciated that the SNR ration can be increased since additional light is collected for each displacement.

The embodiments described herein also facilitate iterative reconstruction based on PMI and OLCR/OCT of eye parameters taking into account optical path of OLCR measurement beam through reconstructed eye.

The reconstruction of ocular surfaces based on multiple OCT measurement points within the eye coordinate system and the alignment of multiple scans using PMI provides for more accurate reconstruction through the use of the detected peaks.

PMI modality also provides for time resolved measurement of eye movements $\Delta x$, $\Delta y$, $\Delta z$, $\Theta$, $\rho$, $\delta$.

It should be appreciated that various techniques described herein may therefore be used to design lenses, for example, including lens implants. The techniques may apply to designing various types of lenses, including, but not limited to: plano, convex, concave, multifocal (refractive, diffractive, etc), toric, accommodative, prismatic, multiple lens configurations, variable curvature (e.g. aspherical), phakic intraocular lenses, light adjustable lenses or any combination of those listed.

Additionally one or more of the techniques described herein may be used in the context of planning or performing various types of surgeries. Such surgeries may include, but are not limited to, myopic, hyperopic and presbyopic LASIK, LASEK or PRK, conductive keratoplasty, radial keratotomy or a combination of the above.

It should be appreciated that the various aspects described above are not limited to human eyes, but rather may be applied to any type of eye, including human eyes or any other organism. In addition, while various aspects have been described as relating to the structure of the eye and implants for the eye, it should be appreciated that the techniques may also apply to additional elements, such as glasses, contact lenses or other elements used for ocular purposes.

As previously mentioned, it should be appreciated that the methods and apparatus described above may be used to form a model of any number of structures of interest within an eye. For example, according to some embodiments, a complete model of the eye may be formed. In other embodiments, a model of a single structure (e.g., the lens, or a surface of the lens) may be formed. In still other embodiments, the methods and/or apparatus described above may be used to determine a single parameter of interest of a structure.

Thus, individual acts of the methods described above may be used for some applications, irrespective of whether the other acts are also performed.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be genetically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In this respect, it should be appreciated that one implementation of the embodiments of the present technology comprises at least one computer-readable storage medium (e.g., a computer memory, a floppy disk, a compact disk, a tape, a flash drive, etc.) encoded with a computer program (i.e., a plurality of instructions), which, when executed on a processor, performs the above-discussed functions of the embodiments of the present technology. The computer-readable storage medium can be transportable such that the program stored thereon can be loaded onto any computer resource to implement the aspects of the present technology discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology.

While various inventive embodiments have been described and illustrated herein, those of ordinary skill in the art will readily envision a variety of other means and/or structure for performing the function and/or obtaining the results and/or one or more of the advantages described herein, and each of such variations and/or modifications is deemed to be within the scope of the inventive embodiments described herein. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present technology are directed to each individual feature, system, article, material, kit, and/or method described herein. In addition, any combination of two or more such features, systems, articles, materials, kits, and/or methods, if such features, systems, articles, materials, kits, and/or methods are not mutually inconsistence, is included within the inventive scope of the present disclosure. All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternative (i.e., "one or the other but not both") when preceded by terms of exclusivity, such as "either," "one of," "only one of," or "exactly one of." "Consisting essentially of," when used in the claims, shall have its ordinary meaning as used in the field of patent law. As used herein the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The words "comprises/comprising" and the words "having/including" when used herein with reference to the present invention are used to specify the presence of stated features, integers, steps or components but does not preclude the presence or addition of one or more other features, integers, steps, components or groups thereof. It is appreciated that certain features of the invention, which are for clarity, described in the context of separate embodiments, may also be provided in combination in a single embodiment. Conversely, various features of the invention which are, for brevity described in the context of a single embodiment, may also be provided separately or in any suitable combination

The invention claimed is:

1. An apparatus for motion compensated modelling of a parameter of an eye, comprising:
   a light source for illuminating a targeted ocular surface with a least one incident light beam and directing at least two light beams returning from the illuminated targeted ocular surface to an image forming device;
   an imaging device for measuring a plurality of position parameters of the eye with respect to an optical reference coordinate system of the apparatus based on an image formed in the image forming device;
   an Optical Coherence Tomography (OCT) device for directing an OCT imaging beam at the targeted ocular surfaces for measuring an interference signal associated with the OCT imaging beam at a plurality of optical reference coordinates, wherein the measurement of the plurality of position parameters and measurement of the interference signal are time synchronized;
   a controller comprising a processor and a computer-readable containing instructions which, when executed by the processor, cause the controller to correct the interference signal to account for a displacements of a parameter of the plurality of position parameters and modelling the eye parameter based at least in part on the corrected interference signal.

2. The apparatus according to claim 1, wherein the plurality of position parameters include one or more of a lateral displacement along an x axis of the optical reference coordinate system, lateral displacement along a y axis of the optical reference coordinate system and axial displacement along a z axis of the optical reference coordinate system.

3. The apparatus according to claim 1, wherein the plurality of position parameters include cyclorotation around the z-axis.

4. The apparatus according to claim 1, wherein the plurality of position parameters include rotation around the x axis and rotation around the y axis.

5. The apparatus according to claim 1, wherein measuring a plurality of position parameters includes interpolating between measurements of the plurality of position parameters.

6. The apparatus according to claim 1, wherein the instructions further cause the controller to determine a reference location of the second measuring device and correct said reference location based on the measured position parameters.

7. The apparatus according to claim 1, wherein the instructions further cause the controller to correct an optical path length based on a difference in an optical path length between an off-axis ray-traced path length and a path length along the z axis of the optical reference coordinate system.

8. The apparatus according to claim 1, wherein the imaging device measures a position parameter based on a retinal reflex.

9. The apparatus according to claim 7, wherein the instructions further cause the controller to iteratively correct the optical path length.

10. The apparatus according to claim 1, wherein the ocular surface includes one or more of an anterior corneal surface, a posterior corneal surface, an anterior lens surface, a posterior lens surface or a retinal surface.

11. The apparatus according to claim 10, wherein the imaging device is selected from a list including a Purkinje Mirror Imaging device, an Optical coherence Tomography Device or a Scheimpflug Imaging System.

12. The apparatus according to claim 10, wherein the instructions further cause the controller to determine refraction at the ocular surface and correct the modelled eye parameter based on the determined refraction.

13. The apparatus of claim 12, wherein the instructions further cause the controller to correct the interference signal to account for a displacement of a parameter of the plurality of position parameters by correcting for an optical path difference associated with the interference signal using the determined refraction.

* * * * *